(12) United States Patent
Crowley

(10) Patent No.: US 9,675,656 B2
(45) Date of Patent: Jun. 13, 2017

(54) BUCCAL AND SUBLINGUAL CANNABINOID FORMULATIONS AND METHOD OF MAKING THE SAME

(71) Applicant: Kenneth L Crowley, Temecula, CA (US)

(72) Inventor: Kenneth L Crowley, Temecula, CA (US)

( * ) Notice: Subject to any disclaimer, the term of this patent is extended or adjusted under 35 U.S.C. 154(b) by 64 days.

(21) Appl. No.: 14/754,160

(22) Filed: Jun. 29, 2015

(65) Prior Publication Data

US 2015/0374770 A1 Dec. 31, 2015

Related U.S. Application Data

(60) Provisional application No. 62/018,484, filed on Jun. 27, 2014.

(51) Int. Cl.
| | |
|---|---|
| *A61K 36/185* | (2006.01) |
| *A61K 31/05* | (2006.01) |
| *A61K 31/352* | (2006.01) |
| *A61K 45/06* | (2006.01) |
| *A61K 9/00* | (2006.01) |
| *A61K 36/534* | (2006.01) |

(52) U.S. Cl.
CPC ............ *A61K 36/185* (2013.01); *A61K 9/006* (2013.01); *A61K 31/05* (2013.01); *A61K 31/352* (2013.01); *A61K 36/534* (2013.01); *A61K 45/06* (2013.01)

(58) Field of Classification Search
CPC ..................................................... A61K 36/00
USPC ......................................................... 424/725
See application file for complete search history.

(56) References Cited

U.S. PATENT DOCUMENTS

| | | |
|---|---|---|
| 2004/0138293 A1 | 7/2004 | Werner et al. |
| 2005/0153931 A1 | 7/2005 | Jarho et al. |
| 2008/0181942 A1 | 7/2008 | Zajicek |
| 2010/0008985 A1 | 1/2010 | Pellikaan et al. |
| 2014/0166027 A1 | 6/2014 | Fuisz et al. |

OTHER PUBLICATIONS

PCT International Search Report and Written Opinion of the International Searching Authority for International Application No. PCT/US2015/038132 (10 pages).

*Primary Examiner* — Michael Meller
(74) *Attorney, Agent, or Firm* — Kilpatrick Townsend & Stockton LLP

(57) ABSTRACT

A cannabinoid troche including polyethylene glycol (or other base ingredients such as gelatin and/or pectin) and oils of peppermint, ginger, citrus, mango, etc., that is administered buccally and/or sublingually. This dosage form demonstrates an improved efficacy with reduced side effects when compared to formulations of cannabinoids in capsules, oral solutions, tinctures, sprays and edibles. The troches avoid harmful preservatives (e.g., BHT, BHA), heavy metals and stabilizers while addressing sub-therapeutic dosing and optimizing the synergistic qualities of the ratios of the individual cannabinoids, terpenes and flavonoids. The use of peppermint oil (and others) in the troche shows improved efficacy above and beyond that which is expected or seen without its use. The troches further allow for accurate and reproducible therapeutic effects with ease of dosage adjustments.

15 Claims, No Drawings

BUCCAL AND SUBLINGUAL CANNABINOID FORMULATIONS AND METHOD OF MAKING THE SAME

CROSS-REFERENCE

This application claims priority to U.S. patent application Ser. No. 62/018,484 filed Jun. 27, 2014 and which is incorporated herein for any and all purposes.

FIELD OF THE INVENTION

The embodiments of the present invention relate to the delivery of cannabinoids via lozenge or troche.

BACKGROUND

Cannabis, commonly known as marijuana and by numerous other names, is a preparation of the cannabis plant intended for use as a psychoactive drug and as medicine. Pharmacologically, the principal psychoactive constituent of cannabis is tetrahydrocannabinol (THC) representing one of hundreds of known compounds in the plant, including many other cannabinoids, such as cannabidiol (CBD), cannabinol (CBN), tetrahydrocannabivarin (THCV) and cannabigerol (CBG).

While certain of the cannabinoids are known to help with certain medical conditions, the illegality of cannabis has prevented wide spread usage for medical conditions. On the other hand, recreational, illegal use has flourished. However, as more and more states legalize cannabis for medical use, there is a need to develop cannabis for the efficient and effective treatment of many medical conditions.

Many cannabis-based products contain harmful preservatives (e.g., BHT, BHA) and stabilizers, artificial flavorings, colors, as well as toxic byproducts (e.g., Benzene, Hexane, heavy metals, etc.) from extraction methods, and/or trigger side effects and fail to provide effective relief for the subject medical condition.

It would be advantageous to develop an efficient and effective cannabis-based product that overcomes the drawbacks associated with currently available cannabis-based products.

SUMMARY

Accordingly, the embodiments of the present invention comprise a cannabinoid lozenge or troche comprising polyethylene glycol (or other bases such as gelatin, pectin, fatty acids (e.g., MBK), waxes, etc.) and oils of peppermint (or other oils and extracts) which is administered buccally and/or sublingually. This dosage form demonstrates an improved efficacy with reduced side effects when compared to formulations of cannabinoids in capsules, oral solutions, tinctures, sprays and edibles. The embodiments of the present invention avoid harmful preservatives (e.g., BHT, BHA) and stabilizers, avoiding artificial sweeteners and colors, while addressing sub-therapeutic dosing and optimizing the synergistic qualities of the ratios of the individual cannabinoids, terpenes and flavonoids. Moreover, embodiments of the present invention allow for accurate and reproducible therapeutic effects with ease of dosage adjustments. It is important to recognize that the troche is able to be accurately cut into as small as $1/16^{th}$ of a dose, allowing broad dosage range adjustment from a single troche.

Other variations, embodiments and features of the present invention will become evident from the following detailed description, drawings and claims.

DETAILED DESCRIPTION

For the purposes of promoting an understanding of the principles in accordance with the embodiments of the present invention, reference will now be made to the embodiments illustrated in the drawings and specific language will be used to describe the same. It will nevertheless be understood that no limitation of the scope of the invention is thereby intended. Any alterations and further modifications of the inventive feature illustrated herein, and any additional applications of the principles of the invention as illustrated herein, which would normally occur to one skilled in the relevant art and having possession of this disclosure, are to be considered within the scope of the invention claimed.

The embodiments of the present invention are useful for the treatment and prevention of a wide range of disorders, including, for example, inflammatory bowel disease (IBS), Crohn's disease (CD), irritable bowel syndrome (IBS), ulcerative colitis (UC), nausea, vomiting, anorexia, cachexia, all forms of pain (i.e. acute, chronic, neuropathic, etc.), gastrointestinal tract distress (i.e. heartburn, indigestion, stomachache, etc.), migraine headaches, postmenstrual syndrome (PMS), Cancer, neurodegenerative diseases like Lou Gehrig's disease, Huntington's disease, Alzheimer's dementia, Parkinson's disease and Parkinsonian-type symptoms, spinal-cord injuries; HIV/AIDS, agitation, insomnia, depression, muscle spasms, spasticity from multiple sclerosis, glaucoma, Autism Spectrum Disorder (ASD), Attention Deficit Hyperactivity Disorder (ADHD), Post-Traumatic Stess Disorder (PTSD), and anxiety disorders. The actives used in the embodiments of the present invention affect the human physiology in positive ways including the improvement of the immune system, prevention or treatment of certain cancers, and reduction of inflammation. Those skilled in the art will recognize that the embodiments of the present invention may be used to treat any and all medical conditions that respond favorably thereto.

The effects of the following cannabinoids: CBD, CBDA, CBG, CBGA, CBC, CBCA, Delta-9 THCA, Delta-9 THC and/or Delta-8 THC, as well as the very important group of physiologically active compounds called terpenes and flavonoids need to be present at certain percentages to optimize the clinical effects on each type of symptom and/or disease for which the product is being used. The embodiments of the present invention also recognize the importance of the ratios of each of the aforementioned actives. These cannabinoids are also temperature sensitive and the embodiments of the present invention recognize the significance of temperature during each relevant step of making the product. For instance, keeping the temperature controlled along with the amount of the acid form of THC and/or CBD may have a profound effect on certain conditions mentioned earlier.

Some of the drawbacks associated with prior art cannabinoid formulations surround the route of administration and the dosage form used. Ease of dosage adjustment is a critical component with the use of cannabis as a treatment. The delivery system disclosed herein offers easy adjustment of the dose needed by the patient, which improves the overall outcome of the use of cannabis therapy.

The embodiments of the present invention are directed to a dosage form that is solid at room temperature. In one embodiment, the dosage form is a lozenge or troche. In either instance, the product may be refrigerated or frozen without harm. Advantageously, with a melting point of approximately >38° C. (100.4° F.), the lozenge or troche dissolves at body temperature within the mouth of a user where the majority of absorption takes place resulting in optimizing the dose absorbed and avoiding the variables of oral absorption and first pass metabolizm.

Formulation begins by combining polyethylene glycol with approximate molecular weights of 1300 to 1650 g/mol with specific forms of gum acacia, citric acid, stevia extract powder, oils of peppermint, menthol and cream de mint at specific temperatures with a range of cannabis extracts providing specific doses that include the following compositions singularly or in combination: (i) Delta-9 Tetrahydrocannabinol in the decarboxylated form in doses ranging from 5 mg to 240 mg (0.5% to 25.26% by weight); (ii) Tetrahydrocannabinolic acid (THC-A in the natural, non-decarboxylated form) in doses of 5 mg to 240 mg (0.5% to 25.26% by weight); (iii) Cannabidiol (CBD) in doses of 5 mg to 240 mg with a Delta-9 THC content less than or equal to 0.3 mg (making this dosage form legal in all states of the United States); and Cannabidiol (CBD) in doses of 5 mg to 240 mg (0.5 to 21.26% by weight) in combination with Delta-9 Tetrahydrocannabinol in a 53:1 ratio (CBD:THC), or down to a ratio of 0.001:1 (CBD:THC), of Delta-9 THC in the decarboxylated and non-decarboxylated forms at specific temperatures. Another possible active includes Delta-8 Tetrahydrocannabinol. Other oils such as sweet orange oil, ginger oil, mango, tangerine, etc., may be substituted or used in combination with oils of peppermint, menthol and cream de mint. The dosage range may increase to 500 mg with the use of pure Cannabidiol or Tetrahydrocannabinol (i.e., crystals).

Temperature control is necessary in the processing of cannabis extracts. As a result, the embodiments of the present invention recognize and use temperatures necessary to optimize cannabinoid, terpene and flavonoid content and ratios. Temperatures in the range of approximately −109° F. to 212° F. (at normal atmospheric pressure; temperatures change with negative pressures which allow for extraction and processing using different methods), maintain certain percentages of all cannabinoids and retain natural terpene and flavonoid content in the extracts thereby resulting in more medicinal value being retained instead of isolating one active. Notwithstanding the importance of the natural mixture of actives, it has been recognized in the instant embodiments of the present invention that one active can be used in the troche providing its own unique physiologic and clinical value.

Depending on the embodiment, Cannabis, C. sativa, C. indica, C. ruderalis and hybrids in the raw material are used to create specific ratios of CBD to THC. Percentages range from 24000:1 CBD:THC (i.e., 240 mg CBD to 0.01 mg THC) to 1:24000 CBD:THC (i.e., 0.01 mg CBD to 240 mg THC). In another embodiment, percentages range 200,000:1 CBD:THC and 1:200,000 CBD:THC.

The embodiments of the present invention contemplate dosage forms with a total weight of between approximately 0.5 grams and 2.01 grams, depending on the formulation of the actives, size of the lozenge or troche. This dosage form can be used for all natural, semi-synthetic and synthetic derivatives of all cannabinoids. Handling and processing of the extract is significant in the proper delivery of the actives with the associated terpenes and flavonoids, all which synergistically work to improve the medicinal value of the cannabinoids chosen for the particular ailment under treatment.

Assembly of the lozenge or troche comprises: (i) preparing a proprietary base of polyethylene glycol with molecular weights of 1300 to 1650 g/mol, gum acacia, stevia extract, citric acid and Magnasweet® (formed of base products comprising Monoammonium Glycyrrhizinate and Ammonium Glycyrrhizinate) by melting the same at a temperature of approximately 58° C. to 64° C. at normal atmospheric pressure; (ii) adding the desired cannabis extract in amount based on the goals of the dosage per troche, symptom treatment or disease state treatment (e.g., 20 mg CBD dose with 1-2 mg of THC is effective for treating patients with autism, arthritis, and seizures); (iii) adding desired essential oils based on the treatment goals, flavoring and/or allergy avoidance; and (iv) adding solution to a lozenge or troche mold device to deliver accuracy of dosage desired. Range of standard deviation is <5% in weight and less than 10% stated active goals.

An exemplary method of producing 900 troches comprises: (i) measuring 670 grams of PEG 1450 (or PEG 1500 +/− PEG 300) (the 670 grams of PEG makes up approximately 75% to 90% total weight); (ii) melting the 670 grams of PEG to a maximum temperature of approximately 60° C.-70° C. (many devices work; stir/hot plate, heated mix/pump/delivery automation—if used under vacuum, temperatures will be lower under automation assembly lines); (iii) once the PEG is melted, adding powders (citric acid—0.17% to 1.2% by weight, stevia (or Luo Han Gou)—0.46% to 3.1% by weight, acacia gum—0.08% to 2.0%, and Magnasweet®—0.02% to 0.06% by weight) and mixing until suspended uniformly; (iv) adding 1 mg to 500 mg of active CBD and THC to each troche in ratios of 24000:1 to 1:1500 (e.g., for a 5 mg troche add 2.5 mg of CBD and 2.5 mg of THC if a 1:1 ratio is desired and add 4.6875 mg of CBD and 0.325 mg of THC if a 15:1 ratio is desired. For a 240 mg troche add 120 mg of CBD and 120 mg of THC for a 1:1 ratio and 225 mg of CBD and 15 mg of THC if a 15:1 ratio is desired) (v) adding 26.22 ml of essential oils (e.g., 20.2 ml of peppermint, 4.6 ml of menthol (made by dissolving 10 gm menthol crystals into 6 ml of peppermint oil and 2 ml of 99.9% ETOH) and 1.5 ml of cream de mint, and mixing to uniformity (the concentration of active oil extract is variable to determine total volume of oil and base to be added); (vi) maintaining temperature between approximately 58° C. and 63° C.; (vii) once completely mixed using a micro pipette to deliver 900 micro liters per troche (for the dosage form of 0.9725 gm/troche); and (viii) allowing mixture to cool at room temperature.

Another exemplary method of producing 900 troches each including 60 mg of THC with approximately 4 mg of CBD comprises: (i) measuring 772 gm of PEG 1450 (or PEG 1500 +/− PEG 300) (the PEG makes up approximately 87% of total weight, based on a 62.5% THC oil containing 5.1% CBD); (ii) melting the 772 gm of PEG to a maximum temperature of approximately 60° C.-70° C. (many devices work; stir/hot plate, heated mix/pump/delivery automation—if used under vacuum, temperatures will be lower under automation assembly lines); (iii) once the PEG is melted, adding 86.4 gm stated concentration cannabis extract oil; (iv) adding a mixed set of powders (citric acid—0.17% to 1.2% by weight, stevia (or Luo Han Gou)—0.46% to 3.1% by weight, acacia gum—0.08% to 2.0% by weight, and Magnasweet®—0.02% to 0.06% by weight) and mixing until suspended uniformly; (v) adding 10 ml of essential organic oils (e.g., 9.7 ml sweet orange oil and 0.3 ml organic peppermint oil); (vi) mixing to uniformity, maintaining temperature between approximately 58° to 63° C.; (vii) once completely mixed using a micro pipette to deliver 900 micro liters per troche (for the dosage form of 0.9725 gm/troche); and (viii) allowing mixture to cool at room temperature.

Another exemplary method of producing 120 gelatin-based troches that are 40 mg total (24 mg CBD and 16 mg CBD) using a 500 mg THC/CBD per gram concentration cannabis extract oil comprises: (i) measuring 122.5 gm gelatin (special gelatin base making up approximately 91% of total weight, again depending on extract concentration) and melting (many different methods to melt) to a temp of approximately 34° C.-40° C.; (ii) once melted, adding 7.2 grams of active (based on stated concentration) using a sir/hot plate or other mixing device including a closed automated injection system, (iii) adding a mixed set of powders (in approximate amounts of the following: Stevia (or Luo Han Gou)—0.25% to 0.45% by weight, acacia gum—0.6% to 1.1% by weight, citric acid—0.5% to 0.8% by weight, Magnasweet® 0.04% to 0.06% by weight and silica—0.32% to 0.81% by weight) and mixing until suspended uniformly; (iv) adding organic essential oils (e.g. orange oil 1.0% to 1.3%, peppermint oil 0.02% to 0.04%); (v) mixing to uniformity, maintaining temperature between approximately 34° C.-40° C.; (vi) once completely mixed using a micro pipette to deliver 900 micro liters per troche (for the dosage form of 1.089 gm/troche); and (vii) allowing mixture to cool at room temperature. Pectin may also be used to produce the troches. Polysaccharides formed of pectin or gelling agents can modify the density of the gelatin troche are in the range of 20,000 to 400,000 g/mol molecular weight. As set forth above, the gelatin-based troche may also include Silica Gel or Silicon Dioxide for purposes of dispersing ingredients.

It will be recognized by those skilled in the art that the formulations set forth above, are exemplary such that variations fall within the spirit and scope of the present invention. For example, the amount of oil used may vary based on concentration. More specifically, when using 560 mg THC/1 gm oil versus 764 mg THC/1 gm oil, the PEG base volume changes appropriately to maintain volume and correct dose, but density and weight changes. Moreover, different oils may be used in different amounts. For example, ginger is a potent oil such that a few drops may suffice whereas other oils may be used in units of milliliters. The combinations of oils may also differ. For example, a formulation may include peppermint oil but no extra menthol or cream de mint while another formulation may use ginger, orange and mint oil. That is, the oils provide a desired level of flavoring in addition to the therapeutic value of oils (e.g., peppermint oil). In addition, while not having the desired flavor, the troche can be made using the PEG, gelatin, pectin, fatty acid and/or wax base and cannabis extract only. Or in another embodiment, the troche can be made using the PEG, gelatin, pectin, fatty acid and/or wax base, cannabis extract and oil only. Or in another embodiment, the troche can be made using the PEG, gelatin, pectin, fatty acid and/or wax base, cannabis extract and one or more of the following: gum acacia, citric acid, stevia extract powder, Luo Han Gou or, Monoammonium Glycyrrhizinate and Ammonium Glycyrrhizinate.

The embodiments of the present invention demonstrate an improved efficacy that is unexpected compared to utilizing the same dose of the same active source of cannabis oil. In one particular example, the formulation comprising PEG and high dose mint oil formula provides unexpected results as described herein.

In one embodiment, a high concentration (99%-99.9%) CBD derived from hemp is used to achieve the desired ratio. In other embodiments, the ratios are determined by the strain of cannabis that includes different amounts of CBD and THC.

The embodiments of the present invention avoid the traditional pitfalls of medicating with other orally ingested cannabinoids such as capsules, elixirs, infused food products, sprays, etc., and topically applied agents. Being a pharmaceutical product, the lozenge or troche provides clear separation from the confusion associated with traditional preparations of natural cannabinoid infused products, including candy bars, chocolate, butter, baked goods, etc., that produce unreliable and varied clinical responses that are not always the same or reproducible. The use of the lozenge or troche offers a method of reduced variability in the pharmacokinetics of the cannabinoids resulting in clinical outcomes that are consistent from dose to dose.

Although the invention has been described in detail with reference to several embodiments, additional variations and modifications exist within the scope and spirit of the invention as described and defined in the following claims.

I claim:

1. A troche for treating a disorder selected from inflammation and pain, the troche consisting essentially of therapeutically effective amounts of polyethylene glycol, cannabis extract, citric acid, gum acacia, and stevia extract.

2. A troche for treating a disorder selected from inflammation and pain, the troche consisting essentially of therapeutically effective amounts of gelatin, cannabis extract, citric acid, gum acacia, and stevia extract.

3. A troche for treating a disorder selected from inflammation and pain, the troche consisting essentially of therapeutically effective amounts of pectin, cannabis extract, citric acid, gum acacia, and stevia extract.

4. A troche for treating a disorder selected from insomnia, post-traumatic stress disorder, and anxiety, the troche consisting essentially of therapeutically effective amounts of polyethylene glycol, cannabis extract, citric acid, gum acacia, and stevia extract.

5. A troche for treating a disorder selected from insomnia, post-traumatic stress disorder, and anxiety, the troche consisting essentially of therapeutically effective amounts of gelatin, cannabis extract, citric acid, gum acacia, and stevia extract.

6. A troche for treating a disorder selected from insomnia, post-traumatic stress disorder, and anxiety, the troche consisting essentially of therapeutically effective amounts of pectin, cannabis extract, citric acid, gum acacia, and stevia extract.

7. A troche for treating a disorder selected from Parkinson's disease, Alzheimer's disease, Autism Spectrum Disorder, and seizures, the troche consisting essentially of therapeutically effective amounts of polyethylene glycol, cannabis extract, citric acid, gum acacia, and stevia extract.

8. A troche for treating a disorder selected from Parkinson's disease, Alzheimer's dementia, Autism Spectrum Disorder and seizures, the troche consisting essentially of therapeutically effective amounts of gelatin, cannabis extract, citric acid, gum acacia, and stevia extract.

9. A troche for treating a disorder selected from Parkinson's disease, Alzheimer's dementia, Autism Spectrum Disorder and seizures, the troche consisting essentially of therapeutically effective amounts of pectin, cannabis extract, citric acid, gum acacia, and stevia extract.

10. The troche of claim 1, wherein said polyethylene glycol is selected from the group consisting of polyethylene glycol 1450 and polyethylene glycol 1500.

11. The troche of claim 1, wherein the cannabis extract has a ratio of cannabidiol to tetrahydrocannabinol in a range of 24000:1 to 1:24000.

12. The troche of claim 1, wherein said cannabis extract consists essentially of one or more of the following: (i) Delta-9 Tetrahydrocannabinol in the decarboxylated form; (ii) Tetrahydrocannabinolic acid in the natural, non-decarboxylated form; (iii) Cannabidiol with a Delta-9 THC content less than or equal to 0.3 mg/g; and Cannabidiol in combination with Delta-9 Tetrahydrocannabinol in a 2% to 6% ratio of decarboxylated and non-decarboxylated forms and (iv) Delta-8 Tetrahydrocannabinol.

13. The troche of claim 1, wherein the cannabidiol is at a concentration of 99%-99.9% in the cannabis extract.

14. The troche of claim 1, wherein the cannabis extract consists essentially of one or more of the following: cannabinoids, terpenes and flavonoids.

15. The troche of claim 1, wherein the pain disorder is selected from the group consisting of acute, chronic, neuropathic or migraine headache pain.

* * * * *

UNITED STATES PATENT AND TRADEMARK OFFICE
CERTIFICATE OF CORRECTION

Page 1 of 1

PATENT NO. : 9,675,656 B2
APPLICATION NO. : 14/754160
DATED : June 13, 2017
INVENTOR(S) : Kenton L Crowley It is certified that error appears in the above-identified patent and that said Letters Patent is hereby corrected as shown below:

On the Title Page

Item (71) Applicant:
Please delete "Kenneth L Crowley" and enter -- Kenton L Crowley --

Item (72) Inventor:
Please delete "Kenneth L Crowley" and enter -- Kenton L Crowley --

Signed and Sealed this
First Day of August, 2017

Joseph Matal
*Performing the Functions and Duties of the*
*Under Secretary of Commerce for Intellectual Property and*
*Director of the United States Patent and Trademark Office*